(12) United States Patent
Nammalwar et al.

(10) Patent No.: US 9,611,237 B2
(45) Date of Patent: Apr. 4, 2017

(54) PHOSPHOR MATERIALS AND RELATED DEVICES

(71) Applicant: GENERAL ELECTRIC COMPANY, Schenectady, NY (US)

(72) Inventors: Prasanth Kumar Nammalwar, Karnataka (IN); Digamber Gurudas Porob, Karnataka (IN); Anant Achyut Setlur, Niskayuna, NY (US); Satya Kishore Manepalli, Karnataka (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/348,244

(22) PCT Filed: Sep. 20, 2012

(86) PCT No.: PCT/US2012/056299
§ 371 (c)(1),
(2) Date: Mar. 28, 2014

(87) PCT Pub. No.: WO2013/048865
PCT Pub. Date: Apr. 4, 2013

(65) Prior Publication Data
US 2014/0231857 A1 Aug. 21, 2014

(30) Foreign Application Priority Data
Sep. 30, 2011 (IN) .......................... 3392/CHE/2011

(51) Int. Cl.
| C09K 11/61 | (2006.01) |
|---|---|
| C09K 11/79 | (2006.01) |
| C09K 11/80 | (2006.01) |
| C09K 11/59 | (2006.01) |
| C09K 11/64 | (2006.01) |
| H01L 33/50 | (2010.01) |
| H01J 61/44 | (2006.01) |
| C07D 301/19 | (2006.01) |
| C09K 11/77 | (2006.01) |
| C07C 1/24 | (2006.01) |
| C07C 5/03 | (2006.01) |
| C07C 29/132 | (2006.01) |
| C07C 407/00 | (2006.01) |

(52) U.S. Cl.
CPC .............. *C07D 301/19* (2013.01); *C07C 1/24* (2013.01); *C07C 5/03* (2013.01); *C07C 29/132* (2013.01); *C07C 407/00* (2013.01); *C09K 11/617* (2013.01); *C09K 11/7721* (2013.01); *C09K 11/7734* (2013.01); *C09K 11/7774* (2013.01); *C09K 11/7792* (2013.01); *H01J 61/44* (2013.01); *H01L 33/502* (2013.01); *C07C 2101/14* (2013.01); *H01L 2224/32245* (2013.01); *H01L 2224/32257* (2013.01); *H01L 2224/48091* (2013.01); *H01L 2224/48247* (2013.01); *H01L 2224/48257* (2013.01); *H01L 2224/49107* (2013.01); *H01L 2224/73265* (2013.01); *H01L 2224/8592* (2013.01); *H01L 2924/181* (2013.01)

(58) Field of Classification Search
CPC .............. C09K 11/0883; C09K 11/616; C09K 11/7721; C09K 11/7734; H01L 33/504
See application file for complete search history.

(56) References Cited

U.S. PATENT DOCUMENTS

| 7,026,755 | B2 | 4/2006 | Setlur et al. | |
|---|---|---|---|---|
| 7,094,362 | B2 | 8/2006 | Setlur et al. | |
| 7,497,973 | B2 * | 3/2009 | Radkov ................ | C09K 11/617 252/301.4 F |
| 7,501,753 | B2 | 3/2009 | Hancu et al. | |
| 7,573,072 | B2 | 8/2009 | Setlur et al. | |

(Continued)

FOREIGN PATENT DOCUMENTS

| CN | 101725847 A | 6/2010 |
|---|---|---|
| CN | 101939857 A | 1/2011 |
| JE | 2011159809 A | 8/2011 |
| JP | 10242513 A | 9/1998 |
| JP | 2003064358 A | 3/2003 |
| JP | 2007048864 A | 2/2007 |
| JP | 2013538253 A | 10/2013 |

OTHER PUBLICATIONS

International Search Report and Written Opinion dated Oct. 12, 2012 which was issued in connection with PCT Patent Application No. PCT/US12/56299 which was filed on Sep. 20, 2012.
Chinese Search Report issued in connection with corresponding CN Application No. 201280047878.X dated Nov. 18, 2014.
Unofficial English Translation of Japanese Office Action issued in connection with corresponding JP Application No. 2014533614 on Jul. 26, 2016.

*Primary Examiner* — Carol M Koslow
(74) *Attorney, Agent, or Firm* — GE Global Patent Operation; Peter T. DiMauro

(57) ABSTRACT

A phosphor material is presented that includes a blend of a first phosphor, a second phosphor and a third phosphor. The first phosphor includes a composition having a general formula of $RE_{2-y}M_{1+y}A_{2-y}Sc_ySi_{n-w}Ge_wO_{12+\delta}:Ce^{3+}$ wherein RE is selected from a lanthanide ion or $Y^{3+}$, where M is selected from Mg, Ca, Sr or Ba, A is selected from Mg or Zn and where $0 \leq y \leq 2$, $2.5 \leq n \leq 3.5$, $0 \leq w \leq 1$, and $-1.5 \leq \delta \leq 1.5$. The second phosphor includes a complex fluoride doped with manganese ($Mn^{4+}$), and the third phosphor include a phosphor composition having an emission peak in a range from about 520 nanometers to about 680 nanometers. A lighting apparatus including such a phosphor material is also presented. The light apparatus includes a light source in addition to the phosphor material.

8 Claims, 4 Drawing Sheets

(56) References Cited

U.S. PATENT DOCUMENTS

| | | |
|---|---|---|
| 2005/0093442 A1* | 5/2005 | Setlur ............... C09K 11/7774 313/512 |
| 2005/0199897 A1 | 9/2005 | Setlur et al. |
| 2006/0016998 A1 | 1/2006 | Ohara |
| 2007/0045650 A1 | 3/2007 | Hancu et al. |
| 2007/0085466 A1 | 4/2007 | Shimomura et al. |
| 2009/0072255 A1 | 3/2009 | Takahashi et al. |
| 2009/0140205 A1 | 6/2009 | Kijima et al. |
| 2009/0236963 A1 | 9/2009 | Nagatomi et al. |
| 2010/0096974 A1 | 4/2010 | Setlur et al. |
| 2010/0142189 A1 | 6/2010 | Hong et al. |
| 2011/0255265 A1 | 10/2011 | Nammalwar et al. |
| 2012/0019126 A1 | 1/2012 | Porob et al. |

* cited by examiner

PHOSPHOR MATERIALS AND RELATED DEVICES

BACKGROUND

The invention relates generally to phosphor blends for wavelength conversion, and specifically phosphor blends for the conversion of radiation emitted by a light source. More particularly, the invention relates to phosphor blends for use with the blue light emitting diodes (LEDs).

A phosphor is a luminescent material that absorbs radiation energy in a portion of the electromagnetic spectrum and emits radiation energy in another portion of the electromagnetic spectrum. One important class of phosphors includes crystalline inorganic compounds of very high chemical purity and of controlled composition to which small quantities of other elements (called "activators") have been added to convert them into efficient fluorescent materials. With the right combination of activators and inorganic compounds, the color of the emission can be controlled. Most useful and well-known phosphors emit radiation (also referred to as light herein) in the visible portion of the electromagnetic spectrum in response to excitation by electromagnetic radiation outside the visible range. For example, the phosphors have been used in mercury vapor discharge lamps to convert the ultra-violet (UV) radiation emitted by the excited mercury to visible radiation. Further, the phosphors may be used in a light emitting diode (LED) to generate colored emissions that may generally not be obtained from the LED itself.

Light emitting diodes (LEDs) are semiconductor light emitters often used as a replacement for other light sources, such as incandescent lamps. They are particularly useful as display lights, warning lights and indicating lights or in other applications where a colored light is desired. The color of light produced by an LED is dependent on the type of the semiconductor material used in its manufacture. The colored LEDs are often used in toys, indicator lights and other devices.

The colored semiconductor light emitting devices, including light emitting diodes and lasers (both are generally referred to as LEDs herein), have been produced from Group III-V alloys such as gallium nitride (GaN). With reference to the GaN-based LEDs, light is generally emitted in the UV and/or blue range of the electromagnetic spectrum. Until quite recently, the LEDs have not been suitable for lighting uses where a bright white light is needed, due to the inherent color of the light produced by the LEDs.

Techniques have been developed for converting the light emitted from the LEDs to useful light for illumination purposes. In one technique, the LED is coated or covered with a phosphor layer. The phosphor absorbs radiation generated by the LED, and generates radiation of a different wavelength, for example, in the visible range of the spectrum.

A combination of LED generated light and phosphor generated light may be used to produce white light. The most popular white LEDs are based on blue emitting GaInN chips. The blue emitting LEDs are coated with a phosphor or a phosphor blend including red, green and blue emitting phosphors that converts some of the blue radiation to a complementary color, for example a yellow-green emission. The total of the light from the phosphor and the LED chip provides white light having a color point with corresponding color coordinates (x and y) and correlated color temperature (CCT), and its spectral distribution provides a color rendering capability, measured by the color rendering index (CRI).

These white LEDs typically produces white light with a CRI between about 70 and about 80 for a tunable CCT greater than about 4000K. While such white LEDs are suitable for some applications, it is desirable to produce white light with higher CRIs (greater than about 90) and lower CCT (less than 3000K) for many other applications.

Therefore, it would be desirable to provide new and improved phosphor blends that produce white light with high CRI and high lumen for low CCT.

BRIEF DESCRIPTION

Briefly, most of the embodiments of the present invention provide a phosphor material that includes a blend of a first phosphor, a second phosphor and a third phosphor. The first phosphor includes a composition having a general formula of $RE_{2-y}M_{1+y}A_{2-y}Sc_ySi_{n-w}Ge_wO_{12+\delta}:Ce^{3+}$, wherein RE is selected from lanthanide ion or $Y^{3+}$, M is selected from the group consisting of Mg, Ca, Sr, Ba and combinations thereof, A is selected from the group consisting of Mg, Zn and combinations thereof; and $0 \le y \le 2$, $2.5 \le n \le 3.5$, $0 \le w \le 1$, and $-1.5 \le \delta \le 1.5$. The second phosphor includes a complex fluoride doped with manganese ($Mn^{4+}$), and the third phosphor include a phosphor composition having an emission peak in a range from about 520 nanometers (nm) to about 680 nanometers (nm).

Some embodiments relate to a lighting apparatus. The lighting apparatus includes a light source; and a phosphor material radiationally coupled to the light source. The light source (e.g., light emitting diode (LED)) is capable of emitting radiation in a range from about 400 nanometers to about 480 nanometers. The phosphor material includes a blend of a first phosphor, a second phosphor and a third phosphor. The first phosphor includes a composition having a general formula $RE_{2-y}M_{1+y}A_{2-y}Sc_ySi_{n-w}Ge_wO_{12+\delta}:Ce^{3+}$, wherein RE a is selected from lanthanide ion or $Y^{3+}$, M is selected from the group consisting of Mg, Ca, Sr, Ba and combinations thereof, A is selected from the group consisting of Mg, Zn and combinations thereof; and $0 \le y \le 2$, $2.5 \le n \le 3.5$, $0 \le w \le 1$, and $-1.5 \le \delta \le 1.5$. The second phosphor includes a complex fluoride doped with manganese ($Mn^{4+}$), and the third phosphor include a phosphor composition having an emission peak in a range from about 520 nm to about 680 nm.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
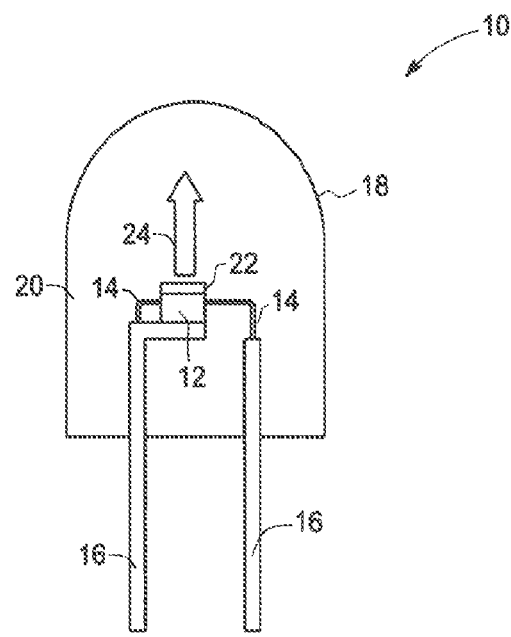
FIG. 1 is a schematic cross sectional view of a lighting apparatus according to one embodiment of the invention.

Approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value.

In the following specification and the claims that follow, the singular forms "a", "an" and "the" include plural referents unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances, an event or capacity can be expected, while in other circumstances the event or capacity cannot occur—this distinction is captured by the terms "may" and "may be".

The terms "first," "second," and the like, herein do not denote any order, quantity, or importance, but rather are used to distinguish one element from another.

As used herein, the term "phosphor" or "phosphor material" or "phosphor composition" may be used to denote both a single phosphor composition as well as a blend of two or more phosphor compositions. The phosphor blend may contain blue, red, yellow, orange and green phosphors. The blue, red, yellow, orange and green phosphors are so called or known after the color of their light emission.

As used herein, the terms "substitution" and "doping" refer to adding an amount of an element in a material. Typically, an element in a material is partially or fully replaced by another element on such addition. It should be noted that various phosphors described herein may be written down by enclosing different elements in parentheses and separated by commas to show substitution or doping, such as in the case of $((Ba,Ca,Sr)_{1-x}Eu_x)_2Si_5N_8$. As understood by those skilled in the art, this type of notation means that the phosphor can include any or all of those specified elements in the formulation in any ratio. That is, this type of notation for the above phosphor, for example, has the same meaning as $((Ba_aCa_bSr_{1-a-b})_{1-x}Eu_x)_2Si_5N_8$, where a and b can vary from 0 to 1, including the values of 0 and 1.

Particular application is described, herein, in conjunction with converting LED-generated ultraviolet (UV), violet, or blue radiation into white light for general illumination purposes. It should be appreciated, however, that the invention is also applicable to the conversion of radiation from UV, violet and/or blue lasers as well as other light sources to white light.

Embodiments of the present techniques provide phosphor blends that may be used in lighting systems to generate white light suitable for general illumination and other purposes. The phosphor blends include a first phosphor of general formula: $RE_{2-y}M_{1+y}A_{2-y}Sc_ySi_{n-w}Ge_wO_{12+\delta}:Ce^{3+}$, wherein RE is selected from lanthanide ion or $Y^{3+}$, M is selected from the group consisting of Mg, Ca, Sr, Ba, and combinations thereof, A is selected from the group consisting of Mg, Zn, and combinations thereof; and $0 \leq y \leq 2$, $2.5 \leq n \leq 3.5$, $0 \leq w \leq 1$, and $-1.5 \leq \delta \leq 1.5$. In one embodiment, the first phosphor may also be represented by general formula of $(RE_{1-x-z}Sc_xCe_z)_2M_{3-p}A_pSi_{n-w}Ge_wO_{12+\delta}$, wherein RE is selected from lanthanide ion or $Y^{3+}$, M is selected from the group consisting of Mg, Ca, Sr, Ba, and combinations thereof, A is selected from the group consisting of Mg, Zn, and combinations thereof; and $0 \leq x \leq 1$, $0 \leq z \leq 0.3$, $0 \leq p \leq 2$, $2.5 \leq n \leq 3.5$, $0 \leq w \leq 1$, and $-1.5 \leq \delta \leq 1.5$. Advantageously, the phosphors made according to these formulations may maintain high emission intensity (quantum efficiency) across a wide range of temperatures. The phosphors may be used in lighting systems, such as LEDs and fluorescent tubes, among others, to produce blue and blue/green light.

In some embodiments, the first phosphor may have general formula of $(Ca_{1-z}Ce_z)_3Sc_2Si_{n-w}Ge_wO_{12}$, where $0 < z \leq 0.3$. Specific embodiments of the first phosphor include the compositions where the Si, Ge component includes at least about 66% $Si^{4+}$, at least about 83% $Si^{4+}$, and 100% $Si^{4+}$. Thus some specific embodiments include $(Ca_{1-z}Ce_z)_3Sc_2(Si_{1-c}Ge_c)_3O_{12}$ where c is from 0.67 to 1.

These phosphors of above formula, have reduced quenching of the luminescence at high temperatures (thermal quenching) as compared to many current phosphors, for example YAG:Ce. Accordingly, these phosphors maintain their emission intensity across a large range of temperatures, which may mitigate losses of intensity or lamp color shifts as the temperature of a lighting system increases during use.

The phosphor blends, further include a second phosphor that is a red line emitter and a third phosphor that has a peak emission in a broad wavelength range from about 520 nm to about 680 nm. The second phosphor may be a complex fluoride that is a line emitter and generates red light. Suitable examples include complex fluorides doped with $Mn^{4+}$, for example $(Na, K, Rb, Cs, NH_4)_2[(Ti, Ge, Sn, Si, Zr, Hf)F_6]:Mn^{4+}$ and the like. In certain instances, a complex fluoride doped with $Mn^{4+}$ is $K_2[SiF_6]:Mn^{4+}$ ("PFS") used in some illustrative blend examples further below.

The third phosphor may include a phosphor composition having an emission peak in a range from about 520 nanometers (nm) to about 680 nm. The third phosphor is usually a yellow or a yellow-orange phosphor having broad emission range. Non-limiting examples of suitable third phosphors may include a garnet, a nitride, and an oxynitride. Table 1 shows some of such examples. Any combination having two or more members selected from the group consisting of a garnet, a nitride, and an oxynitride may also be used.

In some embodiments, the third phosphor may be a garnet of general formula $(A, Ce)_3M_{5-a}O_{12-3/2a}$, wherein $0 \leq a \leq 0.5$, A is selected from the group consisting of Y, Gd, Tb, La, Sm, Pr, Lu, and combinations thereof and M is selected from the group consisting of Sc, Al, Ga, and combinations thereof. An example of such garnet is $Y_3Al_5O_{12}:Ce^{3+}$ (YAG). This garnet YAG has an emission peak in a broad wavelength range from about 525 nm to about 645 nm.

In some embodiments, the third phosphor may be a nitride of general formula $(A, Eu)_xSi_yN_z$, wherein $2x+4y=3z$, and A comprises Ba, Ca, Sr, or a combination thereof. The nitride may be further doped with cerium. Some embodiments include $A_2Si_5N_8:Eu^{2+}$, wherein A comprises Ba, Ca, or Sr. In certain instances, the nitride is of formula $((Ba, Ca, Sr)_{1-a-b}Eu_aCe_b)_2Si_5N_8$, where $0 \leq a \leq 1$ and $0 \leq b \leq 1$. These nitrides emit in broad wavelength range from about 575 nm to about 675 nm.

In some embodiments, the third phosphor may be an oxynitride phosphor of general formula $A_pB_qO_rN_s$: R, where A comprises barium, B comprises silicon, and R comprises europium; and $2<p<6$, $8<q<10$, $0.1<r<6$, $10<s<15$. In these instances, A may further comprises strontium, calcium, magnesium, or a combination thereof; B may further comprise aluminum, gallium, germanium, or a combination thereof; and R may further comprise cerium. In certain instances, the oxynitide phosphor is of formula $(Ba, Ca, Sr, Mg)_4Si_9O_rN_{14.66-(2/3)r}$: Eu such that r is greater than about 1 and less than or equal to about 4. The emission peak of these oxynitrides emit in wavelength range from about 545 nm to about 645 nm.

TABLE 1

Formulas of the third phosphor used in the phosphor blend

| Name | Formula |
| --- | --- |
| Garnet | $Y_3Al_5O_{12}$:$Ce^{3+}$ |
| Nitride | $((Ba, Ca, Sr)_{1-a-b}Eu_aCe_b)_2Si_5N_8$, where $0 \leq a \leq 1$ and $0 \leq b \leq 1$ |
| Oxynitride | $(Ba, Ca, Sr, Mg)_4Si_9O_rN_{14.66-(2/3)r}$; where $1 < r < 4$ |

Each of the general formulas listed herein is independent of every other general formula listed. Specifically, x, y, z, and other variables that may be used as numeric placeholders in a formula are not related to any usage of x, y, z and other variables that may be found in other formulas or compositions.

When the phosphor material includes a blend of two or more phosphors, the ratio of each of the individual phosphors in the phosphor blend may vary, depending on the characteristics of the desired light output, for example color temperature. The relative amounts of each phosphor in the phosphor blend can be described in terms of spectral weight. The spectral weight is the relative amount that each phosphor contributes to the overall emission spectrum of the device. The spectral weight amounts of all the individual phosphors and any residual bleed from the LED source should add up to 100%. In a preferred embodiment, each of the above described phosphors in the blend will have a spectral weight ranging from about 1 percent to about 70 percent.

The relative proportions of each phosphor in the phosphor blends may be adjusted, so that when their emissions are blended and employed in a lighting device, there is produced visible light of predetermined ccx and ccy values on the CIE (International Commission on Illumination) chromaticity diagram. As stated, a white light is preferably produced. This white light may, for instance, possess a ccx value in the range of about 0.25 to about 0.55, and a ccy value in the range of about 0.25 to about 0.55.

The phosphors used to make phosphor blends, may be produced by mixing powders of the constituent compounds and then firing the mixture under a reducing atmosphere. Typically, oxygen-containing compounds of the relevant metals are used. For example, the exemplary phosphor $(Ca_{0.97}Ce_{0.03})_3Sc_2Si_3O_{12}$, discussed further in the examples below, may be produced by mixing the appropriate amounts of oxygen-containing compounds of calcium, cerium, scandium, and silicon, and then firing the mixture under a reducing atmosphere. Silicon may also be provided via silicic acid. After firing, the phosphor may be ball milled, or otherwise ground, to break up any conglomerates that may have formed during the firing procedure. The grinding may be performed after all firing steps are completed, or may be interspersed with additional firing steps.

Non-limiting examples of suitable oxygen-containing compounds include oxides, hydroxides, alkoxides, carbonates, nitrates, silicates, citrates, oxalates, carboxylates, tartarates, stearates, nitrites, peroxides and combinations of these compounds. In embodiments containing carboxylates, the carboxylates used may generally have from one to five carbon atoms, such as formates, ethanoates, proprionates, butyrates, and pentanoates, although carboxylates having larger numbers of carbon atoms may be used. The individual phosphor compositions and a blend of these phosphors may be synthesized by any known method, for example as described in U.S. Pat. No. 7,094,362 B2.

Further, the first phosphors, the second phosphors and the third phosphors discussed above may be blended to form a phosphor blend. For example, phosphor blends may be made that contain the first phosphor having the general formula $(Ca_{0.97}Ce_{0.03})_3Sc_2Si_3O_{12}$, the second phosphor having the general formula $K_2[SiF_6]$:$Mn^{4+}$, and the third phosphor of general formula $Y_3Al_5O_{12}$:$Ce^{3+}$ (YAG). An activator ion may be used in these phosphors to obtain the desired emission spectrum. As used herein, the term "activator ion" refers to an ion (for example $Ce^{3+}$) doped in a phosphor that forms luminescent center and is responsible for the luminescence of the phosphor. Such ions may include ions of Pr, Sm, Eu, Tb, Dy, Tm, Er, Ho, Nd, Bi, Yb, Pb, Yb, Mn, Ag, Cu, or any combinations thereof.

In addition to the synthesis procedures discussed above, many of the phosphors that may be used in the blends described herein may be commercially available. For example, the phosphor YAG, used in blend calculations in presently disclosed phosphor blends, may be commercially available.

The phosphors listed above are not intended to be limiting. Any other phosphors, commercial and non-commercial, that form non-reactive blends with the phosphors of the present techniques may be used in blends and are to be considered to be within the scope of the present techniques. Furthermore, some additional phosphors may be used, e.g., those emitting throughout the visible spectrum region, at wavelengths substantially different from those of the phosphors described herein. These additional phosphors may be used in the blend to customize the white color of the resulting light, and to produce sources with improved light quality. In some embodiments, an additional phosphor may be a phosphor of general formula: $((Sr_{1-z}M_z)_{1-(x+w)}A_wCe_x)_3(Al_{1-y}Si_y)O_{4+y+3(x-w)}F_{1-y-3(x-w)}$; wherein $0<x \leq 0.10$ and $0 \leq y \leq 0.5$, $0 \leq z \leq 0.5$, $0 \leq w \leq x$; A is selected from the group consisting of Li, Na, K, Rb, and a combination thereof; and M is selected from the group consisting of Ca, Ba, Mg, Zn, and a combination thereof.

One embodiment of the invention is directed to a lighting apparatus that includes a phosphor blend radiationally coupled to a light source. As used herein, the term "radiationally coupled" means that the elements are associated with each other so that at least part of the radiation emitted from one is transmitted to the other. A combination of the light from the light source and the light from the phosphor blend may be used to produce white light. For example, a white LED may be based on a blue emitting InGaN chip. The blue emitting chip may be coated with the phosphor blend to convert some of the blue radiation to a complementary color, e.g. a yellow-green emission.

Non-limiting examples of lighting apparatus or devices include devices for excitation by light-emitting diodes (LEDs), fluorescent lamps, cathode ray tubes, plasma display devices, liquid crystal displays (LCD's), UV excitation devices, such as in chromatic lamps, lamps for backlighting liquid crystal systems, plasma screens, xenon excitation lamps, and UV excitation marking systems. These uses are meant to be merely exemplary and not exhaustive.

The light emitted from the lighting apparatus may be characterized using any number of standard measurements. This characterization may normalize the data and make the comparison of light emitted by different lighting apparatus easier to determine. For example, the total of the light from a phosphor and from an LED chip provides a color point with corresponding color coordinates (x and y) in the CIE 1931 chromaticity diagram and correlated color temperature (CCT), and its spectral distribution provides a color rendering capability, measured by the color rendering index (CRI). The CRI is commonly defined as a mean value for 8 standard color samples (R1-8), usually referred to as the general Color Rendering Index, or Ra. A higher value for CRI produces a more "natural" appearance for illuminated objects. By definition, an incandescent light has a CRI of 100, while a typical compact fluorescent light may have a CRI of about 82. Further, the luminosity, or apparent brightness, of a source may also be determined from the spectrum of the emitted light. The luminosity is measured as lumens/W-opt, which represents the number of lumens that 1 watt of light having a particular spectral distribution would represent. A higher lumens/W-opt value indicates that a particular source would appear brighter to an observer.

As the light emitted from combined lighting apparatus components is generally additive, the final spectra of phosphor blends and/or lighting apparatus may be predicted. For example, the amount of light emitted from each phosphor in a blend may be proportional to the amount of that phosphor within the blend. Accordingly, the emission spectrum resulting from the blend can be modeled, and the spectral properties, e.g., the CCT, the CRI, color axes (x and y), and 1 m/W-opt may be calculated from the predicted emission spectrum. Various blends that may be made using the phosphors described above are discussed in the examples below.

Referring to the figures now, FIG. 1 illustrates an exemplary LED based lighting apparatus or lamp 10 that may incorporate the phosphor blends of the present techniques. The LED based lighting apparatus 10 includes a semiconductor UV or visible light source, such as a light emitting diode (LED) chip 12. Power leads 14 that are electrically attached to the LED chip 12 provide the current that causes the LED chip 12 to emit radiation. The leads 14 may include thin wires supported on thicker package leads 16 or the leads may comprise self-supported electrodes and the package lead may be omitted. The leads 14 provide current to the LED chip 12 and thus cause the LED chip 12 to emit radiation.

The lamp 10 may include any semiconductor blue or UV light source that is capable of producing white light when its emitted radiation is directed onto the phosphor. In one embodiment, the semiconductor light source comprises a blue emitting LED doped with various impurities. Thus, the LED 12 may comprise a semiconductor diode based on any suitable III-V, II-VI or IV-IV semiconductor layers and having an emission wavelength of about 380 to 550 nm. In particular, the LED may contain at least one semiconductor layer comprising GaN, ZnSe or SiC. For example, the LED may comprise a nitride compound semiconductor represented by the formula $In_iGa_jAl_kN$ (where $0 \le i$; $0 \le j$; $0 \le k$ and $i+j+k=1$) having an emission wavelength greater than about 380 nm and less than about 550 nm. Preferably, the chip is a near-UV or blue emitting LED having a peak emission wavelength from about 400 to about 500 nm. Such LED semiconductors are known in the art. The light source as described herein is an LED for convenience. However, as used herein, the term is meant to encompass all semiconductor light sources including, e.g., semiconductor laser diodes.

In addition to inorganic semiconductors, the LED chip 12 may be replaced by an organic light emissive structure or other light sources. Other types of light sources may be used in place of LEDs, such as the gas discharge device discussed with respect to FIG. 5, below. Examples of gas discharge devices include low-, medium-, and high-pressure mercury gas discharge lamps.

The LED chip 12 may be encapsulated within a shell 18, which encloses the LED chip and an encapsulant material 20 (also referred to as "encapsulant"). The shell 18 may be glass or plastic. The encapsulant 20 may be an epoxy, plastic, low temperature glass, polymer, thermoplastic, thermoset material, resin, silicone, silicone epoxy, or any other type of LED encapsulating material. Further, the encapsulant 20 may be a spin-on glass or some other high index of refraction material. Typically, the encapsulant material 20 is an epoxy or a polymer material, such as silicone. The shell 18 and the encapsulant 20 are transparent, that is substantially optically transmissive, with respect to the wavelength of light produced by the LED chip 12 and a phosphor material 22, such as the phosphor blends of the present techniques. However, if the LED chip 12 emits light that is within the UV spectrum, the encapsulant 20 may only be transparent to light from the phosphor material 22. The LED based lighting apparatus 10 may include an encapsulant 20 without an outer shell 18. In this application, the LED chip 12 may be supported by the package leads 16, or by a pedestal (not shown) mounted to the package leads 16.

The phosphor material 22 is radiationally coupled to the LED chip 12. In one embodiment, the phosphor material 22 may be deposited on the LED chip 12 by any appropriate method. For example, a solvent based suspension of phosphors can be formed, and applied as a layer onto the surface of the LED chip 12. In a contemplated embodiment, a silicone slurry in which the phosphor particles are randomly suspended may be placed over the LED chip 12. Thus, the phosphor material 22 may be coated over or directly on the light emitting surface of the LED chip 12 by coating and drying the phosphor suspension over the LED chip 12. As the shell 18 and the encapsulant 20 will generally be transparent, an emitted light 24 from the LED chip 12 and the phosphor material 22 will be transmitted through those elements. Although not intended to be limiting, in one embodiment, the median particle size of the phosphor material 22 as measured by light scattering may be from about 1 to about 15 microns.

Figure 2:
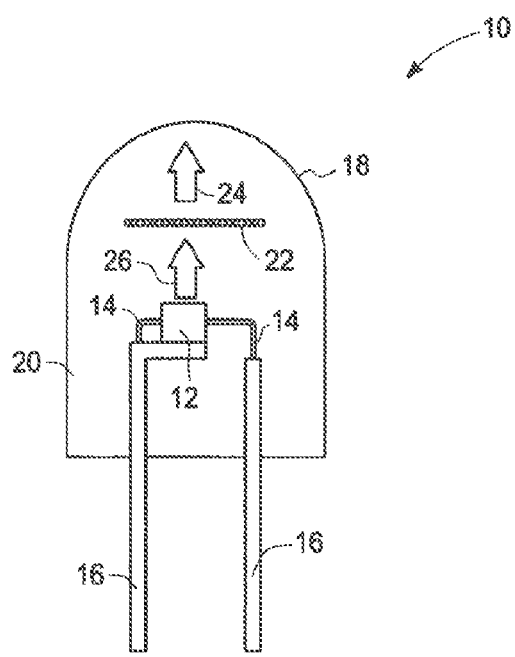
FIG. 2 is a schematic cross sectional view of a lighting apparatus according to one embodiment of the invention.

A second structure that may incorporate the phosphor blends of the present techniques is illustrated in the cross section of FIG. 2. The structure in FIG. 2 is similar to that of FIG. 1, except that the phosphor material 22 is interspersed within the encapsulant 20, instead of being formed directly on the LED chip 12. The phosphor material 22 may be interspersed within a single region of the encapsulant 20 or throughout the entire volume of the encapsulant 20. Radiation 26 emitted by the LED chip 12 mixes with the light emitted by the phosphor material 22, and the mixed light may be visible through the transparent encapsulant 20, appearing as emitted light 24.

The encapsulant 20 with the interspersed phosphor material 22 may be formed by any number of suitable plastics processing techniques. For example, the phosphor material 22 may be combined with a polymer precursor, molded around the LED chip 12, and then cured to form the solid encapsulant 20 with the interspersed phosphor material 22. In another technique, the phosphor material 22 may be blended into a molten encapsulant 20, such as a polycarbonate, formed around the LED chip 12, and allowed to cool. Processing techniques for molding plastics that may be used, such as injection molding, are known in the art.

Figure 3:
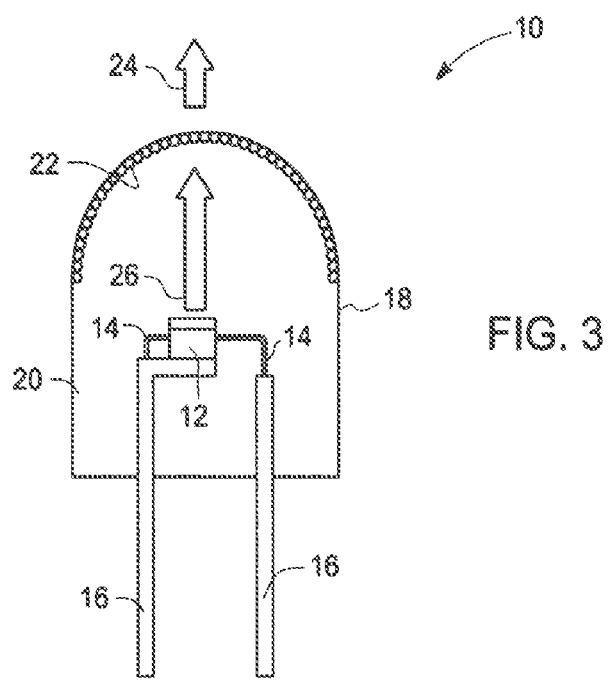
FIG. 3 is a schematic cross sectional view of a lighting apparatus according to one embodiment of the invention.

FIG. 3 illustrates a cross section of a structure that may incorporate the phosphor material 22 of the present techniques. The structure shown in FIG. 3 is similar to that of FIG. 1, except that the phosphor material 22 may be coated onto a surface of the shell 18, instead of being formed over the LED chip 12. Generally, the phosphor material 22 is coated on the inside surface of the shell 18, although the phosphor material 22 may be coated on the outside surface of the shell 18, if desired. The phosphor material 22 may be coated on the entire surface of the shell 18 or only a top portion of the surface of the shell 18. The radiation 26 emitted by the LED chip 12 mixes with the light emitted by the phosphor material 22, and the mixed light appears as emitted light 24.

The structures discussed with respect to FIGS. 1-3 may be combined, with the phosphor material located in any two or all three locations or in any other suitable location, such as separately from the shell or integrated into the LED. Further, different phosphor blends may be used in different parts of the structure.

In any of the above structures, the LED based lighting apparatus 10 may also include a plurality of particles (not shown) to scatter or diffuse the emitted light. These scattering particles would generally be embedded in the encapsulant 20. The scattering particles may include, for example, particles made from $Al_2O_3$ (alumina) or $TiO_2$. The scattering particles may effectively scatter the light emitted from the LED chip 12, and are generally selected to have a negligible amount of absorption.

Figure 4:
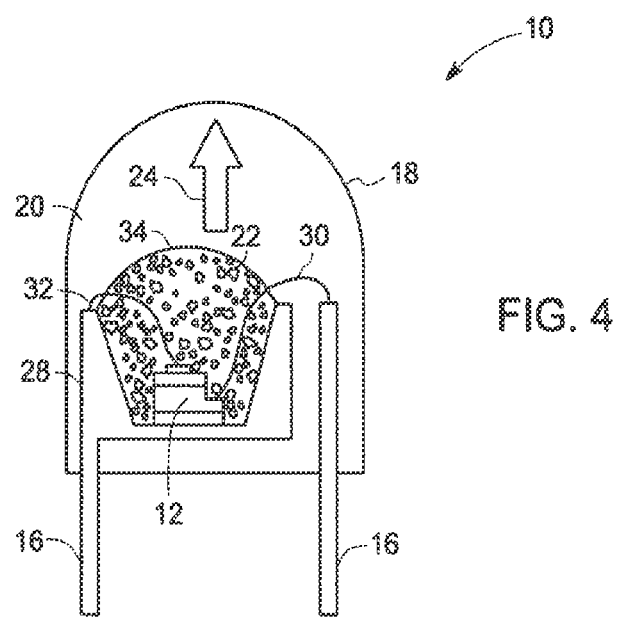
FIG. 4 is a schematic cross sectional view of a lighting apparatus according to one embodiment of the invention.

In addition to the structures above, the LED chip 12 may be mounted in a reflective cup 28, as illustrated by the cross section shown in FIG. 4. The reflective cup 28 may be made from or coated with a reflective material, such as alumina, titania, or other dielectric powder known in the art. Generally, the reflective surface may be made from $Al_2O_3$. The remainder of the structure of the LED based lighting apparatus 10 of FIG. 4 is the same as that of the previous figure, and includes two leads 16, a conducting wire 30 electrically connecting the LED chip 12 with one of the leads 16, and an encapsulant 20. The reflective cup 28 may conduct current to energize the LED chip 12, or a second conducting wire 32 may be used for the same. The phosphor material 22 may be dispersed throughout the encapsulant 20, as described above, or may be dispersed in a smaller transparent casing 34 formed within the reflective cup 28. Generally, the transparent casing 34 may be made from the same materials as the encapsulant 20. The use of the transparent casing 34 within the encapsulant 20 may be advantageous in that a smaller amount of the phosphor material 22 may be required than if the phosphor were to be dispersed throughout the encapsulant 20. The encapsulant 20 may contain particles (not shown) of a light scattering material, as previously described to diffuse the emitted light 24.

Figure 5:
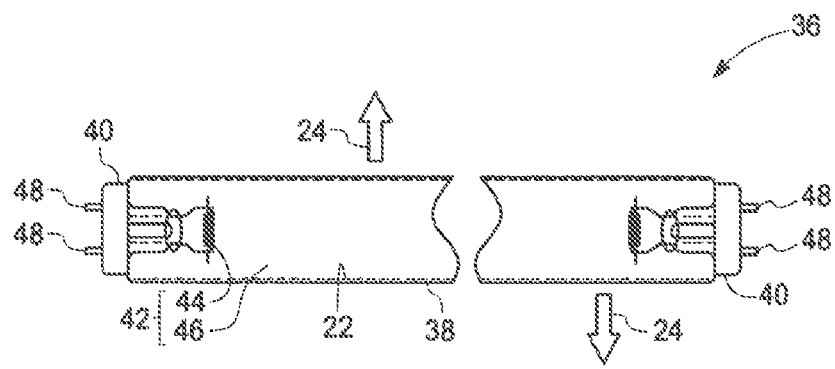
FIG. 5 is a schematic cross sectional view of a lighting apparatus according to one embodiment of the invention.

FIG. 5 is a perspective view of a lighting apparatus 36 based on a gas discharge device, such as a fluorescent lamp, which may use the phosphor blends of the present techniques. The lamp 36 may include an evacuated sealed housing 38, an excitation system 42 for generating UV radiation and located within the housing 38, and a phosphor material 22 disposed within the housing 38. End caps 40 are attached to either end of the housing 38 to seal the housing 38.

In a typical fluorescent lamp, the phosphor material 22, such as the phosphor blends of the present techniques, may be disposed on an inner surface of the housing 38. The excitation system 42 for generating the UV radiation may include an electron generator 44 for generating high-energy electrons and a fill gas 46 configured to absorb the energy of the high-energy electrons and emit UV light. For example, the fill gas 46 may include mercury vapor, which absorbs energy of the high-energy electrons and emits UV light. In addition to mercury vapor, the fill gas 46 may include a noble gas such as argon, krypton, and the like. The electron generator 44 may be a filament of a metal having a low work function (for example, less than 4.5 eV), such as tungsten, or a filament coated with alkaline earth metal oxides. Pins 48 may be provided to supply electrical power to the electron generator 44. The filament is coupled to a high-voltage source to generate electrons from the surface thereof.

The phosphor material 22 is radiationally coupled to the UV light from the excitation system 42. As previously described, radiationally coupled means that the phosphor material 22 is associated with the excitation system 42 so that radiation from the UV light from the excitation system 42 is transmitted to the phosphor material 22. Thus, a phosphor material that is radiationally coupled to the excitation system 42 may absorb radiation, such as the UV light emitted by the excitation system 42, and, in response, emit longer wavelengths, such as blue, blue-green, green, yellow, or red light. The longer wavelength of light may be visible as emitted light 24 transmitted through the housing 38. The housing 38 is generally made of a transparent material such as glass or quartz. Glass is commonly used as the housing 38 in fluorescent lamps, as the transmission spectrum of the glass may block a substantial portion of the "short wave" UV radiation, i.e., light having a wavelength of less than about 300 nm.

A particulate material, such as $TiO_2$ or $Al_2O_3$, may be used in conjunction with the phosphor blend 22 to diffuse light generated by the light source 36. Such a light scattering material may be included with the phosphor blend 22 or separately disposed as a layer between the inner surface of the housing 38 and the phosphor blend 22. For a fluorescent tube, it may be advantageous to have the median size of the particles of the scattering material range from about 10 nm to about 400 nm.

Although the lighting apparatus or the lamp 36 shown in FIG. 5 has a straight housing 38, other housing shapes may be used. For example, a compact fluorescent lamp may have a housing 38 that has one or more bends or is in a spiral shape, with electrical supply pins 48 that are disposed at one end of the lamp 36.

By assigning appropriate spectral weights for each phosphor, one can create spectral blends to cover the relevant portions of color space for white lamps. Specific examples of this are shown below. For various desired CCT's, CRT's and color points, one can determine the appropriate amounts of each phosphor to include in the blend. Thus, one can customize phosphor blends to produce almost any CCT or color point, with corresponding high CRI. Of course, the color of each phosphor will be dependent upon its exact composition (for example relative amounts of Ba, Ca, Sr, as well as Eu in nitride phosphor), which can change the color of the phosphor to a degree where it may have to be renamed. However, determining the changes in the spectral weight to produce the same or similar characteristic lighting device necessitated by such variations is trivial and can be accomplished by one skilled in the art using various methodologies, such as design of experiment (DOE) or other strategies.

By use of the present invention, particularly the blends described in herein, lamps can be provided having high luminosity and general CRI values greater than about 80, for a low range of color temperatures of interest (2500 K to 4000 K) for general illumination. In some blends, the CRI values approach the theoretical maximum of 100. In addition, the $R_9$ value for these blends can exceed about 90 and approach the theoretical maximum as well. Table 1 and Table 2 show luminosity, CRI values and $R_9$ values of various blends at CCT values 2700K and 3000K, respectively.

EXAMPLES

The examples that follow are merely illustrative, and should not be construed to be any sort of limitation on the scope of the claimed invention.

TABLE 2

Formulas of example phosphors used in the phosphor blend

| Name | Formula |
| --- | --- |
| CaSiG | $(Ca_{0.97}Ce_{0.03})_3Sc_2Si_3O_{12}$ |
| PFS | $K_2[SiF_6]:Mn^{4+}$ |
| YAG | $Y_3Al_5O_{12}:Ce^{3+}$ |
| C-BASIN | $Ba_{1.538}Ca_{0.4}Eu_{0.06}Ce_{0.002}Si_5N_8$ |
| YON | $Ba_4Si_9O_4N_{12}:Eu^{2+}$ |
| SASOF | $(Sr_{0.895}Ca_{0.1}Ce_{0.005})_3Al_{0.6}Si_{0.4}O_{4.4}F_{0.6}$ |

TABLE 3

Examples of phosphor blend produced

| Example. | Phosphor blend |
| --- | --- |
| Example 1 | CaSiG/YAG/PFS |
| Example 2 | CaSiG/YON/PFS |
| Example 3 | CaSiG/CBASIN/PFS |
| Example 4 | CaSiG/SASOF/PFS/YAG |

TABLE 4

| S. No. | CCT | Wavelength of LED emission (nm) | Spectral weight of LED emission | Spectral weight of YAG | Spectral weight of PFS | Spectral weight of YON | Spectral weight of CaSiG | Spectral weight of CBASIN | Spectral weight of SASOF | Lumenosity (lumen/watt) | CRI | R9 |
| --- | --- | --- | --- | --- | --- | --- | --- | --- | --- | --- | --- | --- |
| 1 | 2700K | 430 | 0.099 | 0.499 | 0.295 | | 0.106 | | | 320 | 85.9 | 90.7 |
| 2 | | 440 | 0.0805 | 0.527 | 0.297 | | 0.0945 | | | 328 | 87.6 | 92.4 |
| 3 | | 450 | 0.0777 | 0.552 | 0.294 | | 0.0753 | | | 330 | 90.1 | 93.6 |
| 4 | | 440 | 0.0714 | | 0.308 | 0.25 | 0.37 | | | 328 | 94.2 | 94.8 |
| 5 | | 450 | 0.0899 | | 0.273 | 0.232 | 0.404 | | | 330 | 95.8 | 96.9 |
| 6 | | 430 | 0.099 | 0.461 | 0.294 | | 0.094 | | 0.05 | 320 | 85.9 | 90.9 |
| 7 | | 440 | 0.0805 | 0.49 | 0.297 | | 0.826 | | 0.049 | 328 | 87.6 | 92.5 |
| 8 | 3000K | 440 | 0.0921 | | 0.278 | 0.2137 | 0.416 | | | 328 | 92.7 | 97.7 |
| 9 | | 430 | 0.122 | 0.442 | 0.265 | | 0.169 | | | 319 | 85.1 | 87.7 |
| 10 | | 440 | 0.099 | 0.475 | 0.267 | | 0.157 | | | 328 | 87.1 | 89.7 |
| 11 | | 450 | 0.099 | 0.508 | 0.262 | | 0.129 | | | 330 | 90.1 | 91.1 |
| 12 | | 430 | 0.1 | | 0.04 | | 0.34 | 0.58 | | 278 | 94 | 93 |
| 13 | | 440 | 0.08 | | 0.04 | | 0.34 | 0.54 | | 283 | 96 | 94 |
| 14 | | 450 | 0.07 | | 0.03 | | 0.34 | 0.56 | | 284 | 98 | 93 |

Figure 6:
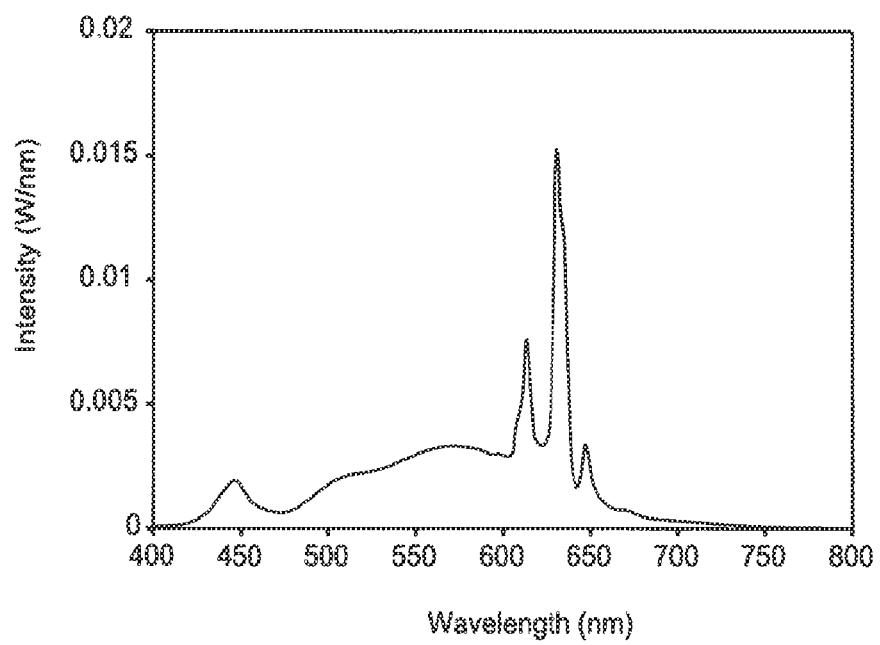
FIG. 6 shows the emission spectra of a phosphor blend using a 450 nm excitation wavelength, in accordance with an exemplary embodiment of the invention.
Figure 7:
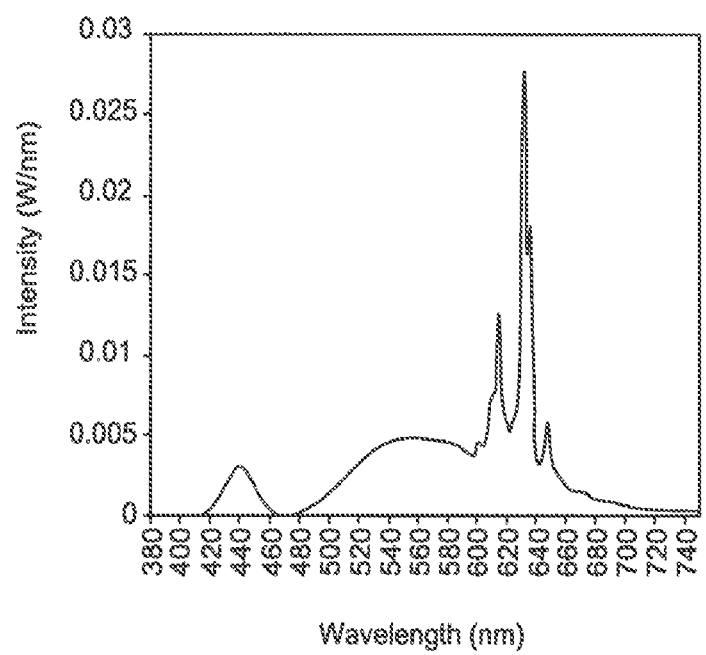
FIG. 7 shows the emission spectra of a phosphor blend using a 450 nm excitation wavelength, in accordance with another exemplary embodiment of the invention.

Various phosphor compositions according to the formulations listed in Table 2, were manufactured. The emission spectra of individual phosphors were obtained, and used in calculations to predict emission spectra for various blends presented in Table 3. Further, the calculations also included any visible light emitted by a light source. FIGS. 6 and 7 show the predicted emission spectra of the examples 1 and 2 of the blends in Table 3. The predicted amount of each phosphor based on spectral weight is shown in the Table 4 along with the spectral contribution of the emissions from the light sources, for example blue LEDs having peak wavelengths of 430 nm, 440 nm and 450 nm. Further, the spectral characteristics calculated from the predicted spectra for these blends are also presented in Table 4. FIGS. 6 and 7 correspond to the blend examples No. 4 and 3, respectively, of Table 4. Advantageously, these blends generate white light having high luminosity, a high CRI value and a low CCT that can be tuned between 2500K and 3000K.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A phosphor material comprising a blend of:
   a first phosphor,
      wherein the first phosphor comprises a composition of general formula $(Ca_{1-z}Ce_z)_3Sc_2Si_{n-w}Ge_wO_{12}$, where $0<z\leq0.3$ and $0\leq w\leq1$, and $2.5\leq n\leq3.5$
   a second phosphor comprising a complex fluoride doped with manganese ($Mn^{4+}$), and
   a third phosphor comprising a phosphor composition having an emission peak in a range from about 520 nm to about 680 nm, wherein the third phosphor comprises a garnet of formula $Y_3Al_5O_{12}:Ce^{3+}$;

wherein when the phosphor material is radiationally coupled to a light source emitting radiation in a range from about 400 nanometers to about 480 nanometers, results in a white light having CCT of from 2500 K to 4000 K, and $R_9$ exceeding about 90.

2. The phosphor material of claim 1, wherein the second phosphor comprises a general formula $A_2[MF_6]:Mn^{4+}$, wherein A is selected from the group consisting of Na, K, Rb, Cs, $NH_4$, and a combination thereof; and M is selected from the group consisting of Si, Ti, Zr, Mn, and a combination thereof.

3. A phosphor material comprising a blend of:
a first phosphor comprising a composition having a general formula of $RE_{2-y}M_{1+y}A_{2-y}Sc_ySi_{n-w}Ge_wO_{12+\delta}$:$Ce^{3+}$, wherein RE is selected from lanthanide ion or $Y^{3+}$, M is selected from the group consisting of Mg, Ca, Sr, Ba, and combinations thereof, A is selected from the group consisting of Mg, Zn, and combinations thereof; and $0 \leq y \leq 2$, $2.5 \leq n \leq 3.5$, $0 \leq w \leq 1$, and $-1.5 \leq \delta \leq 1.5$,
a second phosphor comprising a complex fluoride doped with manganese ($Mn^{4+}$), and
a third phosphor comprising a phosphor composition having an emission peak in a range from about 520 nm to about 680 nm, wherein the third phosphor comprises an oxynitride of a general formula $A_pB_qO_rN_s$: R, where A is barium, B is silicon, and R is europium; and $2<p<6$, $8<q<10$, $0.1<r<6$, $10<s<15$.

4. The phosphor material of claim 3, wherein the second phosphor comprises a general formula $A_2[MF_6]:Mn^{4+}$, wherein A is selected from the group consisting of Na, K, Rb, Cs, $NH_4$, and a combination thereof; and M is selected from the group consisting of Si, Ti, Zr, Mn, and a combination thereof.

5. A phosphor material comprising a blend of:
a first phosphor comprising a composition having a general formula of $RE_{2-y}M_{1+y}A_{2-y}Sc_ySi_{n-w}Ge_wO_{12+\delta}$:$Ce^{3+}$, wherein RE is selected from lanthanide ion or $Y^{3+}$, M is selected from the group consisting of Mg, Ca, Sr, Ba, and combinations thereof, A is selected from the group consisting of Mg, Zn, and combinations thereof; and $0 \leq y \leq 2$, $2.5 \leq n \leq 3.5$, $0 \leq w \leq 1$, and $-1.5 \leq \delta \leq 1.5$,
a second phosphor comprising a complex fluoride doped with manganese ($Mn^{4+}$), and
a third phosphor comprising a phosphor composition having an emission peak in a range from about 520 nm to about 680 nm, wherein the third phosphor comprises $A_2Si_5N_8:Eu^{2+},Ce^{3+}$ wherein A is selected from the group consisting of Ba, Ca, Sr, and a combination thereof.

6. The phosphor material of claim 5, wherein the second phosphor comprises a general formula $A_2[MF_6]:Mn^{4+}$, wherein A is selected from the group consisting of Na, K, Rb, Cs, $NH_4$, and a combination thereof; and M is selected from the group consisting of Si, Ti, Zr, Mn, and a combination thereof.

7. A lighting apparatus comprising: a light source capable of emitting radiation in a range from about 400 nanometers to about 480 nanometers; and the phosphor material of claim 1 radiationally coupled to the light source.

8. The lighting apparatus of claim 7, wherein the light source comprises a light emitting diode (LED).

* * * * *